(12) United States Patent
Tong et al.

(10) Patent No.: US 8,359,123 B2
(45) Date of Patent: Jan. 22, 2013

(54) ROBOTIC SYSTEM AND TRAINING METHOD FOR REHABILITATION USING EMG SIGNALS TO PROVIDE MECHANICAL HELP

(75) Inventors: Kaiyu Tong, Hong Kong (CN); Rong Song, Hong Kong (CN)

(73) Assignee: The Hong Kong Polytechnic University, Hong Kong (CN)

( * ) Notice: Subject to any disclaimer, the term of this patent is extended or adjusted under 35 U.S.C. 154(b) by 1018 days.

(21) Appl. No.: 12/298,887

(22) PCT Filed: Apr. 28, 2007

(86) PCT No.: PCT/CN2007/001433
§ 371 (c)(1),
(2), (4) Date: Feb. 9, 2009

(87) PCT Pub. No.: WO2007/128225
PCT Pub. Date: Nov. 15, 2007

(65) Prior Publication Data
US 2009/0259338 A1 Oct. 15, 2009

(30) Foreign Application Priority Data
Apr. 29, 2006 (CN) .......................... 2006 1 0079973

(51) Int. Cl.
*A61H 1/02* (2006.01)
(52) U.S. Cl. .......... 700/258; 600/546; 600/595; 601/23; 601/33; 700/260; 700/261
(58) Field of Classification Search .................. 600/546, 600/595; 601/5, 33, 34; 607/48; 700/258, 700/260, 261
See application file for complete search history.

(56) References Cited

U.S. PATENT DOCUMENTS

| 5,078,152 A * | 1/1992 | Bond et al. .................... 600/587 |
| 5,466,213 A * | 11/1995 | Hogan et al. .................... 601/33 |
| 5,722,420 A | 3/1998 | Lee |
| 2004/0106881 A1* | 6/2004 | McBean et al. .................... 601/5 |
| 2005/0130815 A1* | 6/2005 | Abdoli-Eramaki .......... 482/121 |

FOREIGN PATENT DOCUMENTS

| WO | 2004050172 | 6/2004 |
| WO | WO 2005087307 A2 * | 9/2005 |
| WO | 2006021952 | 3/2006 |
| WO | 2006039403 | 4/2006 |
| WO | PCT/CN2007/001433 | 8/2007 |

* cited by examiner

*Primary Examiner* — Khoi Tran
*Assistant Examiner* — Stephen Holwerda
(74) *Attorney, Agent, or Firm* — Workman Nydegger

(57) ABSTRACT

A robotic system for rehabilitation using EMG signals to provide mechanical help includes EMG electrodes (6) sequentially connected in series, a DAS card (2) and a control portion (1), and further includes an actuator (3) connected to the DAS card (2) and an additional moment providing portion (4) connected to the actuator (3). The EMG electrodes sense EMG signals corresponding to the muscle of suffering joint, and input the sensed EMG signals to the control portion (1) through the DAS card (2). The control portion (1) uses the input EMG signals and a constant moment set as desired to calculate an additional moment to be applied to the suffering joint, and additional moment providing portion (4) is controlled to apply the corresponding additional moment to the suffering joint through the DAS card (2) and the actuator (3).

10 Claims, 9 Drawing Sheets

ROBOTIC SYSTEM AND TRAINING METHOD FOR REHABILITATION USING EMG SIGNALS TO PROVIDE MECHANICAL HELP

BACKGROUND OF THE INVENTION

1. Field of the Invention

The present invention relates to rehabilitation training equipments for assistant medical treatment, specifically to a rehabilitation robotic system and training method for providing mechanical help by using EMG (electromyographic) signals acquired from patients' affected side.

2. Description of Related Art

Stroke is a common disease. The traditional rehabilitative devices have been introduced by Interactive robotic therapist in U.S. Pat. No. 5,466,213 and A Multiple-motion rehabilitation training robot for hemiplegia upper limbs in Chinese Patent application CN 1480118A, for helping patients training their shoulder-elbow joints. However, the patients can merely be trained passively with these devices within such a little space which patients may not reach for their dyskinesia.

Usually, there are some residual measured EMG signals in the patients' affected muscle, and many of the rehabilitation devices use the residual EMG signals to encourage patients to join the rehabilitation trainings initiatively, such as Myoelectricity trainer disclosed in Chinese Patent CN 2103990U. However, these devices provide only a sound or visual feedback to patients based on the detected EMG signals, while there is no actual machinery help to the patients. This means that the devices could help the patients participate in the rehabilitation in their own initiative, but the acting qualities of the patients are restricted due to their own acting difficulties, so the devices could not help the patients' rehabilitation training in a better way.

BRIEF SUMMARY OF THE INVENTION

The object of this invention is to provide a new rehabilitation training equipment and method to help patients participate in mechanical training initiatively for improving the acting functions.

The main object of this invention is to provide a rehabilitative robotic system for providing mechanical help to patients' affected joints by using biofeedback (EMG signals). This rehabilitative robotic system comprising: an EMG electrode; a data acquisition card (DAS card); a control unit connecting to the EMG electrode and the data acquisition card in series; a driver connecting to the data acquisition card; an additional torque providing unit connecting to the driver, wherein the EMG signals from the muscle corresponding to affected joints are detected by the EMG electrode, and inputted into the control unit via the data acquisition card; and based on the inputted EMG signals and a preset constant torque required for mechanical help, an additional torque to affected joints is calculated by the control unit and further is provided via the data acquisition to the driver; the driver controls the additional torque providing unit with the additional torque for assisting affected joints.

Produced from the muscle of affected joints when the patient act the affected muscle consciously using the rehabilitation robotic system, residual EMG signals is inputted into the control unit via the EMG electrodes, then the control unit controls the additional torque providing unit with the EMG signals to provide a proper additional torque. In the course of training, an assistive constant torque could be provided required for mechanical help by the control unit, which can be an assistive torque has same direction as the patient to act, or a resistive torque has opposite direction with the patient to act.

Preferably, this rehabilitation robotic system further comprising a amplifying and filtering circuit, that is EMG amplifier, for rectifying and amplifying the EMG signals in full-wave, filtering with a moving window, such as with a moving window of 100 ms, and inputting the EMG signals into the data acquisition card. At the same time, the data acquisition card acquires EMG signals and additional torque signals at the sampling frequency of 1000 Hz in real time, and acquires angle signal at the sampling frequency of 100 Hz.

Preferably, a normalized EMG signal $NEMG_j$ inputted in the control unit are attained under the following equation (1):

$$NEMG_j = \frac{w_j - w_r}{w_{mvc} - w_r} \quad (1)$$

wherein, $w_j$ is an amplitude of rectified and filtered EMG signals created by the current acting of patients' affected joints' muscle, $w_r$ is an amplitude rectified and filtered EMG signals created by patients' affected joints' muscle at rest, $w_{mvc}$ is the rectified and filtered maximum amplitude of EMG signals created during maximal voluntary contraction;

the additional torque $T_m$ is calculated by the control unit under the following equation (2):

$$T_m = K_1 \times NEMG_j - K_2 \times NEMG_i + T_0 \quad (2)$$

wherein, $NEMG_j$ is normalized EMG signal of the agonistic muscle, $NEMG_i$ is normalized EMG signal of the antagonistic muscle, $K_1$ is the weighting coefficient of agonistic muscle, $K_2$ is the weighting coefficient of the antagonistic muscle, and $T_0$ is an additional constant torque that provided according to requirement. $T_0$ can be zero, positive value or negative value. The positive values means the direction of the torque and the direction which patients want to move are same, and the negative values means the direction of the torque and the direction which patients want to move are opposite.

Preferably, the rehabilitation robotic system of the present invention further comprising: an angle sensor fixed on the additional torque providing unit and connected to the data acquisition card for measuring a patients' affected joint angle and inputting the angle into the control unit via the data acquisition card; and a display unit connected to the control unit for displaying the information of the patients' affected joint angles and an objective angle to patient. The system can provide mechanical help and visual feedback to patients at the same time for promoting the acting space of patients and improving patients' rehabilitation confidence, further stimulating their cerebral consciousness with the visual feedback.

Preferably, the system further comprising: a mechanical arm fixed on the additional torque providing unit for providing additional torque; and a motor connected to the mechanical arm for rotation, wherein the driver is motor driver. The assistive torque can assist the weak affected muscles accomplish their acting when the patient can not complete the acting by themselves for the mechanical arm connecting to the upper or lower limbs to be trained. Provided with the mechanical arm, the proper resistant torque used in the training can help patients improve their muscle strength when they can finish their acting independently.

Preferably, the system further comprising: a torque sensor fixed on the additional torque providing unit and electrically connected to the data acquisition card for detecting an interactive torque between the mechanical arm and the motor; a first coupling movably connecting the mechanical arm with one end of the torque sensor; and a second coupling connecting the motor with another end of the torque sensor, wherein the torque sensor, the first coupling, the second coupling, the mechanical arm and the motor all share a same axis. For example, the rehabilitation robotic system can apply to patients' elbow joints, wrist joints, knee joints, ankle joints and shoulder joints for rehabilitation training by changing different mechanical arms.

Preferably, three measures are taken to protect patients' training, comprising: mechanical stops for limiting the acting of the mechanical arm is fixed on the additional torque providing part; the control unit will limit the torque which produced by the motor to the preset range, and the operation will be stopped if the torque which produced by the motor exceed the range; an emergency stop is set on the control unit for breaking the power supply to the servo motor.

Another object of this invention is to provide a method using EMG signals to provide mechanical help, the method comprising the steps of: S1 detecting the EMG signals from the muscle corresponding to affected joints by an EMG electrode; S2 inputting the EMG signals into a control unit via a data acquisition card; S3 calculating an additional torque to affected joints basing on the inputted EMG signals and a preset constant torque required for mechanical help by a control unit and further providing the additional torque to a driver via the data acquisition card; S4 controlling an additional torque providing unit to provide the additional torque for assisting affected joints by the driver.

Preferably, the EMG signals can be acquired from corresponding agonistic muscle and antagonistic muscle for different joints.

The rehabilitation robotic system and training method for providing mechanical help to patients using EMG signals of this invention control the assistive torque acting on patients' affected using the residual EMG signals. Meanwhile, visual feedback accompanied by the objective angle and the current angle, which can promote the acting space of the patients' affected joints by mechanical help. The method using EMG signals can strengthen patients' confidence and active practice, and help patients' affected joints rehabilitated fast.

DETAILED DESCRIPTION OF THE INVENTION

Figure 1:
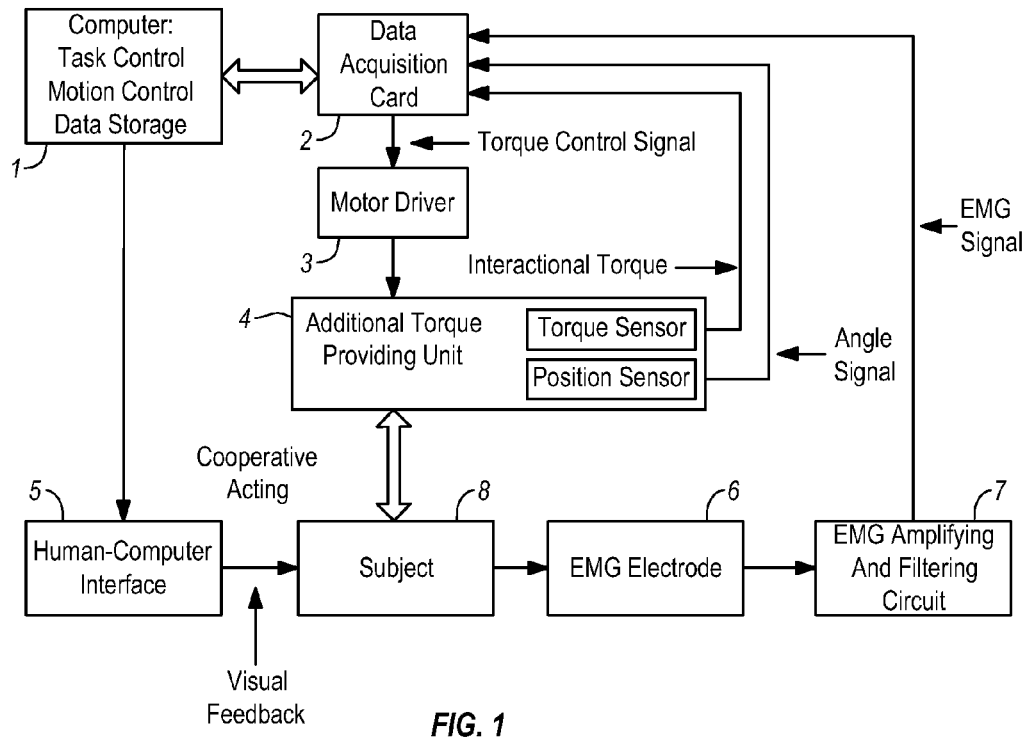
FIG. 1 is a structure diagram of rehabilitation robotic system for providing mechanical help to patients by using EMG signals of the present invention.

The person skilled in the art knows that EMG signals is one-dimensional time series signals and originated motor neurons in spinal cord as a part of the central nervous system and is the sum of action potentials sent by many motor neurons contacted with electrodes. The EMG signals reflect the acting status of muscle and are approximately linear to the force generated from muscle.

Using the approximate linear relationship between EMG signals and the force generated from muscle, the inventors develop a rehabilitation robotic system and a method for providing mechanical help to patients by using EMG signals for overcoming the drawbacks in prior art. This system and method can control the additional torque acting on patients' affected parts by using the EMG signals from affected muscle, such as patients' upper/lower limbs which including elbows, wrists, ankles, knees and shoulders, and accomplish the rehabilitation training cooperate with affected joints for assisting patients self-rehabilitation and promoting the acting space of affected joints, and improving the patients' rehabilitation confidence to improve the rehabilitation effects of the patients.

The additional torque could be produced by a mechanical arm when the patient act on the muscle consciously, and complete the acting with bio-mechanical torque from affected joints for the mechanical arms connecting the upper/lower limbs required to be trained. The mechanical arm can provide assistive torque to help the weak affected muscles accomplish their acting according to the additional torque provided by EMG signals at patients' affected side when patients can not complete the acting by themselves. The mechanical arm also can provide a constant resistive torque to help patients improve their muscle strength when they can finish their acting independently.

In other words, this system and method can make the additional torque (assistive torque or resistive torque) act on patients' affected part mechanically for assisting them carry out the rehabilitation training.

The control strategy of this invention is as follows:

Before sampling, the EMG signals are amplified with a gain of 1,000 times and were band-pass filtered in 10-400 Hz, and then are sampled at 1000 Hz. Then the sampled EMG signals are full-wave rectified and filtered with a moving window of 100 ms. Electromechanical delay, which exited between the EMG signals and the mechanical torque generated by the muscle, was assumed to be 50 ms in the literature. The moving window could also cause a delay of 50 ms to the processed EMG signals in real time, which would cause the synchronization between the torque generated by the motor and the torque generated by the muscle.

Later, a normalized EMG signal $NEMG_j$ is attained under the following equation (1):

$$NEMG_j = \frac{w_j - w_r}{w_{mvc} - w_r} \quad (1)$$

Wherein, $w_j$ is the amplitude of rectified and filtered EMG signals created by the current acting of patients' affected joints' muscle, $w_r$ is the amplitude of rectified and filtered EMG signals created by patients' affected joints' muscle at rest, $w_{mvc}$ is the rectified and filtered maximum amplitude of EMG signals created during maximal voluntary contraction.

Later, the additional torque $T_m$ which the mechanical arms need to be provided is attained under the following equation (2):

$$T_m = K_1 \times NEMG_j - K_2 \times NEMG_i + T_0 \qquad (2)$$

Wherein, $NEMG_j$ is normalized EMG signals of the agonistic muscle, $NEMG_i$ is normalized EMG signals of the antagonistic muscle, $K_1$ is weighting coefficient of the agonistic muscle, $K_2$ is weighting coefficient of the antagonistic muscle, and $T_0$ is an additional constant torque that provided according to requirement. $T_0$ can be zero, positive value or negative value. The positive value means the direction of the torque and the direction which patients want to move are same, and the negative value means the direction of the torque and the direction which patients want to move are opposite. By adjusting the values of $K_1$, $K_2$ and constant torque $T_0$, the mechanical arms can give patients different help.

Furthermore, this system has been developed with software in a PC-based platform, and further visual feedback can be provided to patients for guiding patients to complete kinds of training tasks.

The structure of the rehabilitation robotic system for providing mechanical help and visual feedback to patients by using EMG signals of the present invention will be described with reference to FIG. 1 to 9.

FIG. 1 is a structure diagram of rehabilitation robotic system of this invention.

As shown in FIG. 1, the rehabilitation robotic system of the present invention mainly comprises: a PC-based platform (control part) 1 for carrying out the task control, motion control, as well as data storage; a data acquisition card 2 for performing digital-analog and analog-digital conversion and acquiring EMG signals and torque signals, then inputting data to PC after digital-analog and analog-digital conversion, and acquiring angle pulse signals inputting into the computer 1, and inputting the control signal calculated with algorithm into a motor driver 3 after digital-analog and analog-digital conversion; the motor driver 3 for driving motor; an additional torque providing unit 4 comprises: a motor, a torque sensor, an angle sensor (also called position sensor) and a number of auxiliary equipment (the embodiments of additional torque providing unit will be described with reference to FIG. 2 to 9); a human-computer interface 5 connecting to PC for displaying current mission and joint angles to patients, such as a monitor; an EMG electrode 6 affixed to the corresponding muscle; an EMG amplifying and filtering circuit 7 for amplifying and filtering the EMG signals from the EMG electrode 6; patients 8.

As shown in FIG. 1, the present invention constructs a closed loop control system which connected by the cycle of brain-nerve-muscle-computer information processing and control-additional torque providing unit-hemiplegic portion (such as upper/lower limb) acting-feedback interface-nerve-brain. Patients can control the mechanical arms and their own muscle to complete acting together. The mechanical arms can help patients' hemiplegic parts improve acting quality which still controlled by patients' brains, which help patients join the rehabilitation trainings initiatively, and strengthen the confidence of patients for overcoming the problem that the enthusiasm of patients' active participation is difficult to improve in existing rehabilitation training.

Concretely speaking, when patients want to control their own muscle, produced by the muscle, the EMG signals is inputted into the computer 1 via the amplifying and filtering circuit 7 and the data acquisition card 2 by the EMG electrode 6 affixed to the surface of muscle. Simultaneously, the interacting torque between mechanical arm and motor and the angle of patient's training joint are inputted into the computer 1 via the torque sensor, the position sensor and the data acquisition card. Then the computer 1 calculates the torque with equation (1) and (2), and controls the motor to produce corresponding torque. The computer 1 provides several different objective tracks to patients for training with the human-computer interface 5 (such as monitor). The monitor displays the present actual angle and objective angle of patients in real time.

In this way, patients can control their limbs acting coordinated with the mechanical arms, and then self-regulates the EMG signals based on the actual joint angle and objective angle for reducing the gap with the goal and completing the prescriptive action. At the same time, the computer storage EMG signals, torque signals and the angular signals for data analysis and statistics.

In addition, preferably, two computer screens are used, one is placed in front of the patients for guiding the training of patients and the other is placed in front of the operators (such as health care professionals) for controlling the system, such as setting the parameters and monitoring the rehabilitation training with the system.

Figure 2:
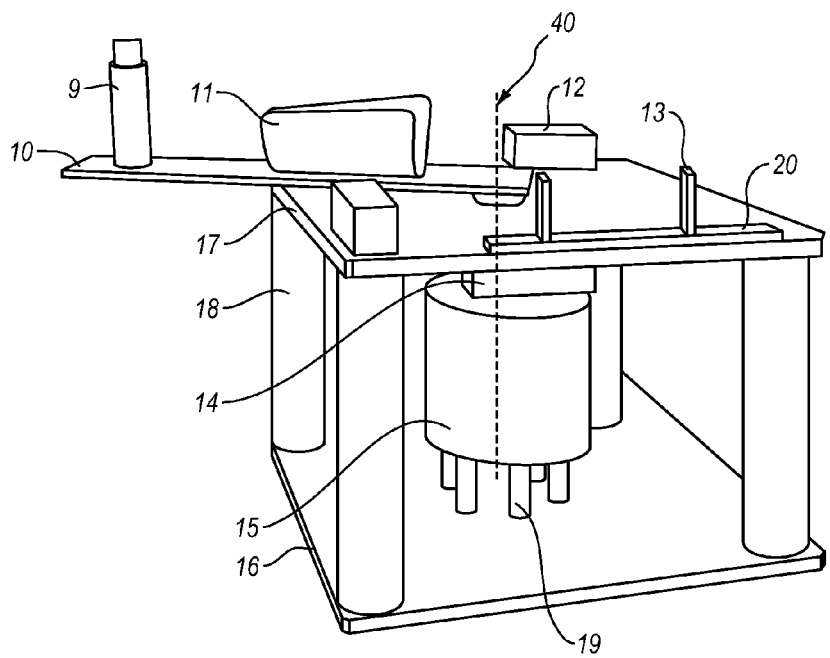
FIG. 2 is a stereo view of additional torque providing unit designed for elbow joints extension and flexion training of the present invention.

FIG. 2 is a stereo view of the additional torque providing unit 4 designed for elbow joints training of the present invention.

The additional torque providing unit 4 mainly comprises: a mechanical arm 10 fixed on a panel 17 for placing forearm, and installed a handle 9 for patients gripping conveniently, a support 11 for fixing the forearm and a tieback 24 (see FIG. 4); a motor 15 with an angle sensor fixed on a bottom plate 16 for rotating the mechanical arm 10 connected to the mechanical arm 10 via a first coupling 21 (see FIG. 3), a torque sensor 22 (see FIG. 3) and the a second coupling 23 (see FIG. 3); a base plate 20 fixed on the panel 17; a bracket 13 fixed on the base plate 20 for supporting patient's upper arm, which could move back and forth to adjust the scope of acting; a mechanical brake 12 fixed on the panel 17 for limiting the movement of mechanical arm 10; a connecting block 14 for connecting the torque sensor 22 and the panel 17; a big support pillar 18 (four) for supporting the panel on the base plate; a small support pillar 19 (six) for fixing the motor 15 on the base plate 16; wherein, the first coupling 21, the second coupling 23, the torque sensor 22, the motor 15 and the mechanical arm 10 shared a same axis. In this way, the support 11 and the mechanical arm 10 can guide the forearm rotate around the axis, and the torque sensor can detect the torque between the motor and the mechanical arm in real time, and the angle sensor can detect the position of the motor rotation in real time, that is the angle of rotation of the affected joint. Wherein, the interaction torque detected by the torque sensor between the mechanical arm and the motor can combine with the EMG signals for various analysis.

Preferably, the motor 15 is a direct drive (DDR) brushless AC servo motor. Driven by a servo driver, the brushless AC servo motor could rotate smoothly at a very low velocity (less than 2 rev/s), and has a flat velocity/torque curve with a high torque output (Nm), which is suitable for the biomechanical acting for human's joints.

Preferably, the angle sensor of motor 15 is an incremental optical shaft encoder fixed on the motor shaft and the practical encoder's resolution for measuring the joint angle can reach 655,360 lines/resolution, which provide the maximum accuracy of the measured joint angle up to 0.00055 degree.

For safety issues, three steps are taken to protect patients during the training. Firstly, two mechanical stops 12 are used to limit the rotation range of the motor 15. Secondly, the control unit limits the torque generated by motor to the preset range with the software program, and the operation will be stopped if the torque generated by motor exceeded the range. The torque that the motor can generate ranged from −5 Nm to 5 Nm. Thirdly, an emergency stop button is set on the PC-based platform for permitting the person who is in charge of the training to use the emergency brake to cut off the power of the servo motor.

Figure 3:
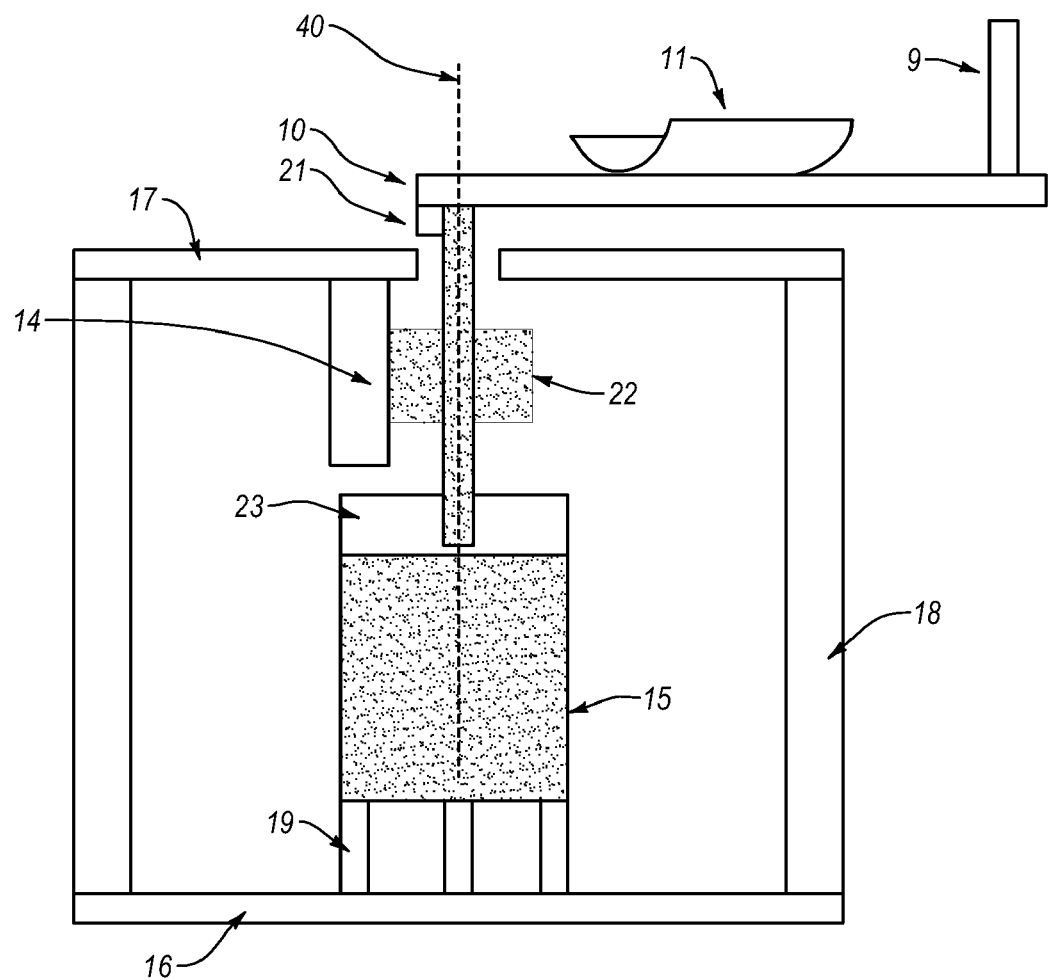
FIG. 3 is a side view of additional torque providing unit designed for elbow joints extension and flexion training of the present invention.

FIG. 3 is a side view of additional torque providing part 4 designed for elbow joints training of the present invention.

FIG. 3 shows the first coupling 21, the torque sensor 22 and the second coupling 23 which are not shown in FIG. 2. Wherein, one side of the torque sensor 22 is connected to the mechanical arm via the first coupling 21, and the other side is connected to motor 15 via the second coupling 23.

Figure 4:
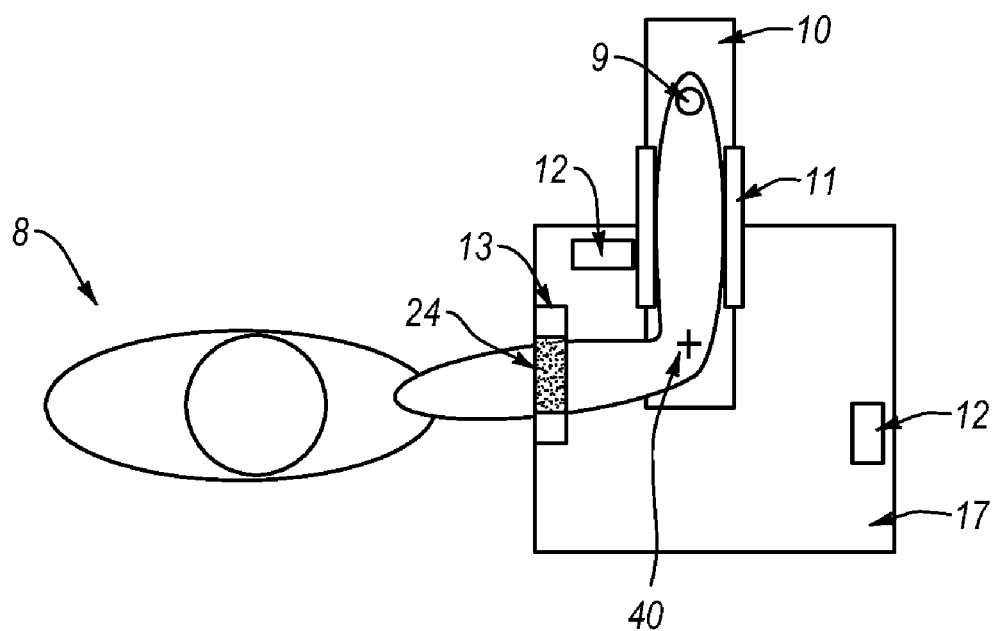
FIG. 4 is a top view of additional torque providing unit designed for elbow joints extension and flexion training of the present invention.

FIG. 4 is a top view of additional torque providing unit 4 designed for elbow joints extension and flexion training of the present invention.

FIG. 4 shows the tieback 24 and a tester 8 which are not shown in FIGS. 2 and 3. Wherein, the tieback 24 is fixed on the bracket 13 to help patient's upper arm fix on the bracket 13. Moreover, patient's forearm is combined with the mechanical arm 10 via the support 11 (see FIG. 3) with semicircular cross section and the tieback 24 which fixes the forearm to the support.

The additional torque providing unit 4 designed for wrist joints, knee joints and ankle joints training will be illustrated with reference to FIG. 5, FIG. 6 and FIG. 7. In order to avoid encumbrance, above that has been described will not be repeated unless it is necessary.

Figure 5:
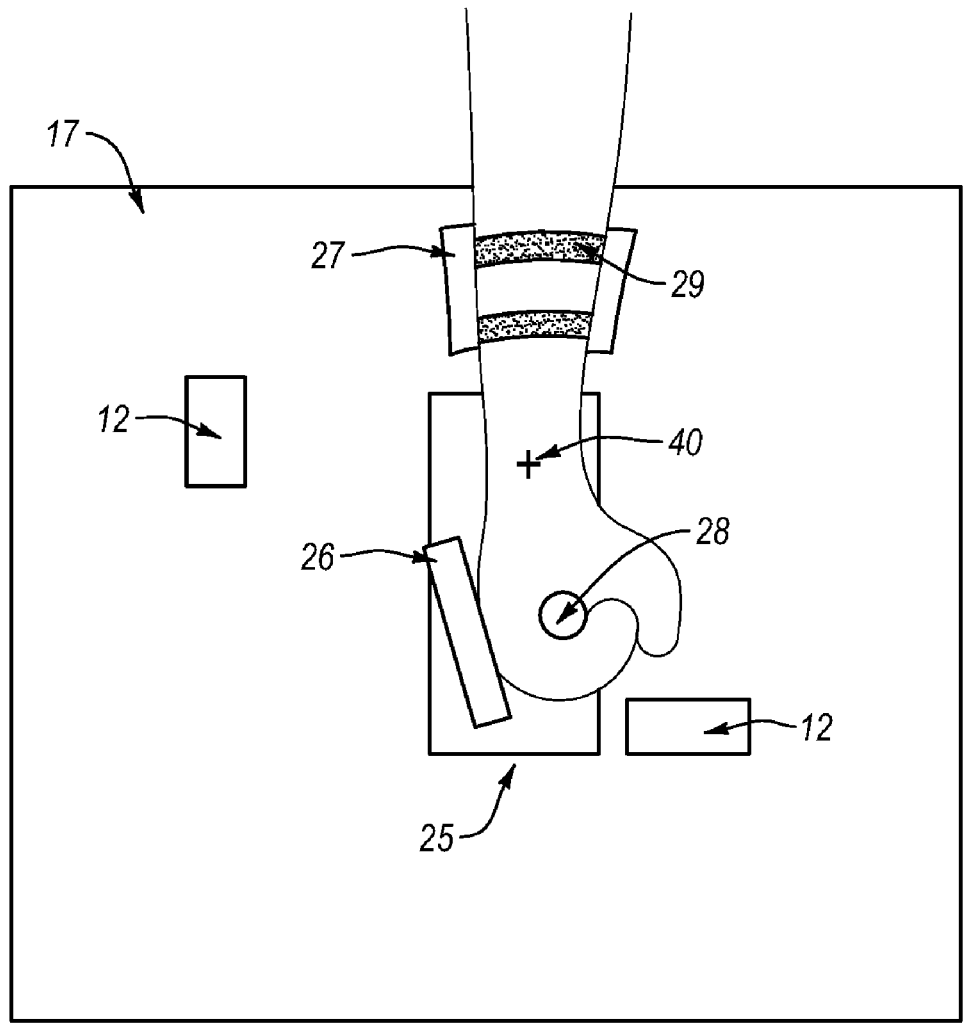
FIG. 5 is a top view of additional torque providing unit designed for wrist joints extension and flexion training of the present invention.

FIG. 5 is a top view of additional torque providing unit 4 designed for wrist joints extension and flexion training of the present invention.

The additional torque providing unit 4 comprises: a mechanical arm 25 designed for training the wrist joint and connected to the first coupling 21 via the nut; a baffle 26 fixed on the mechanical arm 25 for fixing the patient's wrist; a baffle 27 fixed on the panel 17 for fixing the forearm; a handle 28 fixed on the mechanical arm 25 for facilitating patient to grip; a tieback 29 fixed on the baffle 27 for fixing the forearm with the baffle 27; and the axis 40 shared with the first coupling 21, the second coupling 23, the torque sensor 22, the motor 15, the mechanical arm 25 for rotation.

Figure 6:
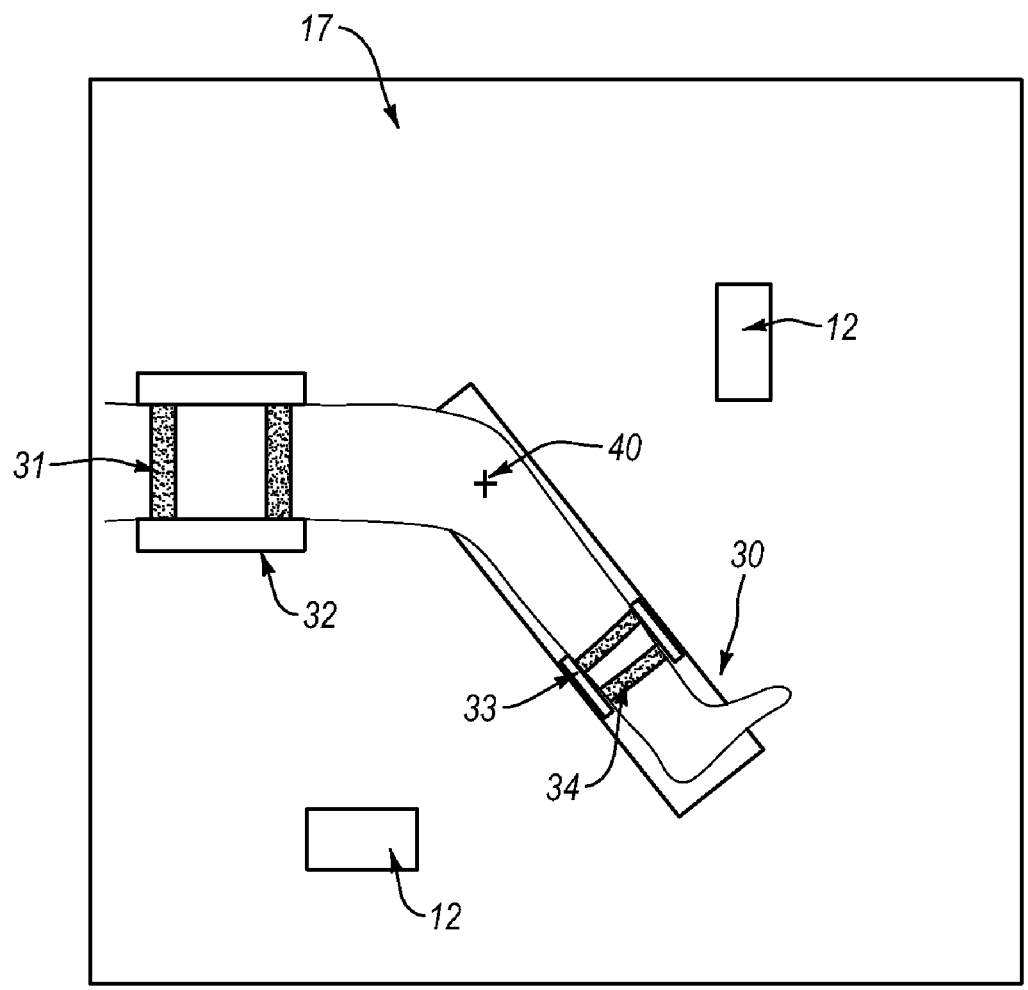
FIG. 6 is a side view of additional torque providing unit designed for knee joints extension and flexion training of the present invention.

FIG. 6 is a side view of additional torque providing unit 4 designed for knee joints extension and flexion training of the present invention.

The additional torque providing unit 4 comprises: a mechanical arm 30 designed for training the knee joint and connected to the first coupling 21 via the nut; a tieback 31; a tieback 31 fixed on a support 32 for fixing patient's thigh with the support together; the support 32 fixed on the panel 17 for fixing patient's thigh; a baffle 33 fixed on the mechanical arm 30 for fixing the patient's calf; a tieback 34 fixed on the baffle 33 for fixing the calf; and the axis 40 shared by the first coupling 21, the second coupling 23, the torque sensor 22, the motor 15, the mechanical arm 30 for rotation.

Figure 7:
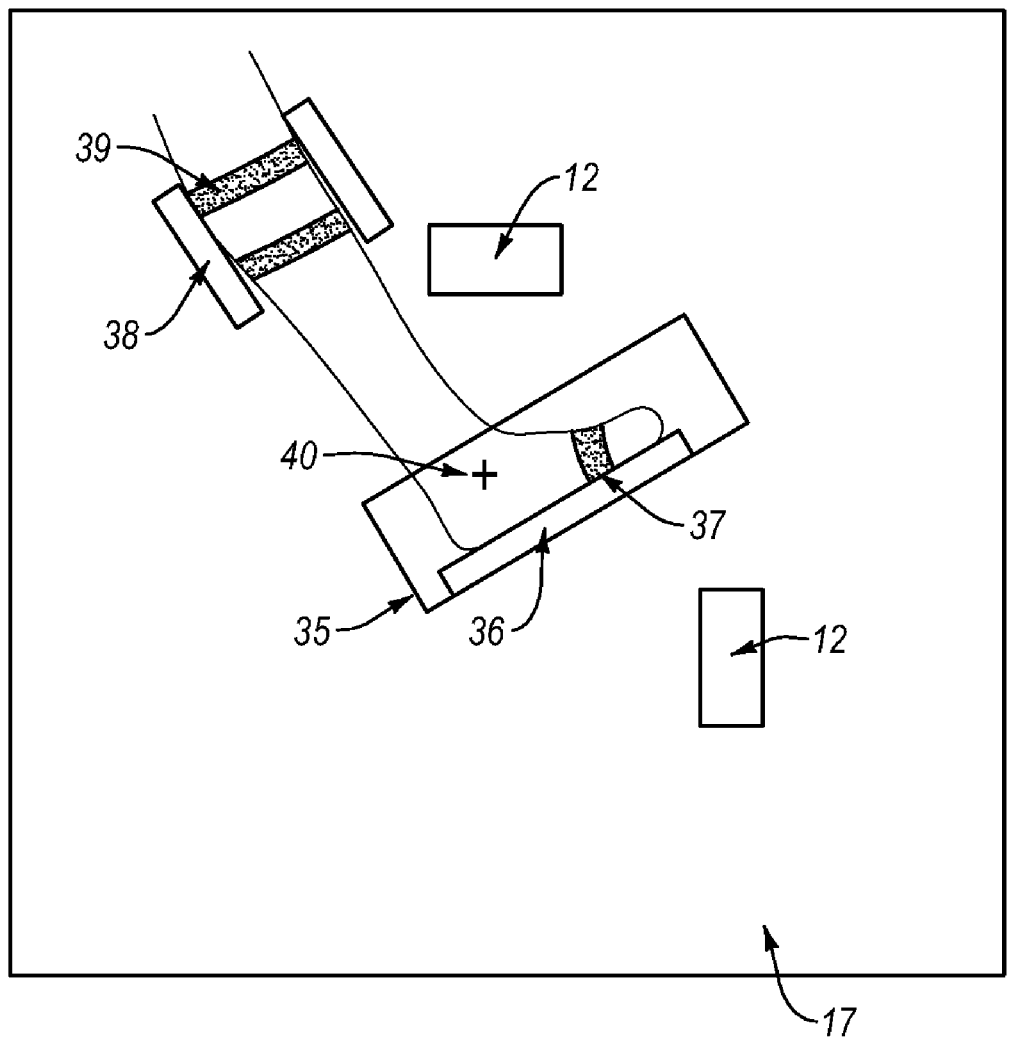
FIG. 7 is a side view of additional torque providing unit designed for ankle joints extension and flexion training of the present invention.

FIG. 7 is a side view of additional torque providing unit 4 designed for ankle joints extension and flexion training of the present invention.

The additional torque providing unit 4 comprises a mechanical arm 35 designed for training the ankle joint and connected to the first coupling 21 via the nut; a support 36 fixed on the mechanical arm 35 for fixing patient's feet; a tieback 37 fixed on the support 36 for fixing patient's feet with the support together; a tieback 39 fixed on the baffle 38, and the baffle 38 fixed on the panel 17 for fixing the patient's calf; and the axis 40 shared by the first coupling 21, the second coupling 23, the torque sensor 22, the motor 15, the mechanical arm 35 for rotation.

Figure 8:
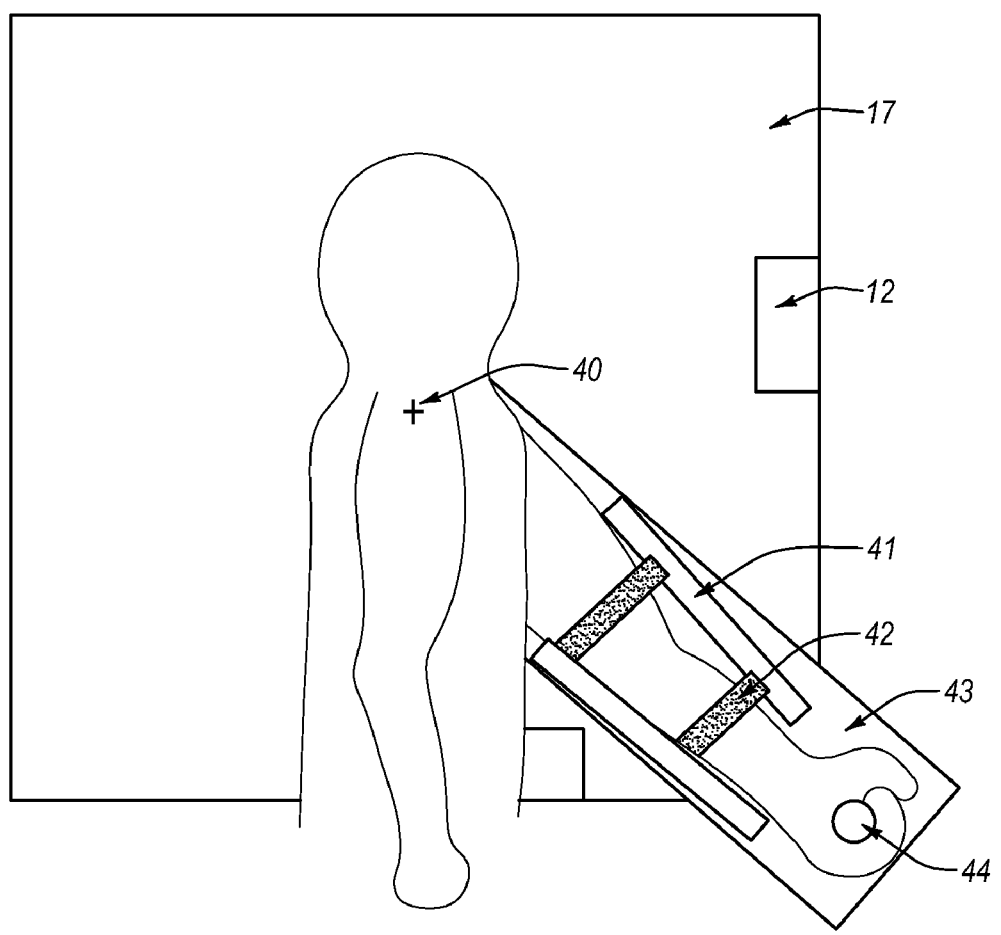
FIG. 8 is a side view of additional torque providing unit designed for shoulder joints anterior flexion and posterior extension training of the present invention.

FIG. 8 is a side view of additional torque providing unit 4 designed for shoulder joints anterior flexion and posterior extension training of the present invention.

The additional torque providing unit 4 comprises: a mechanical arm 43 designed for training the shoulder joint and connected to the first coupling 21 via a nut; a support 41 fixed on the mechanical arm 43 for fixing patient's upper arm and forearm; a tieback 42 fixed on the support 41 for fixing patient's upper arm and forearm with the support together; a handle 44 fixed on the mechanical arm 43 for facilitating patient to grip; and the axis 40 shared by the first coupling 21, the second coupling 23, the torque sensor 22, the motor 15, the mechanical arm 43 for rotation.

Figure 9:
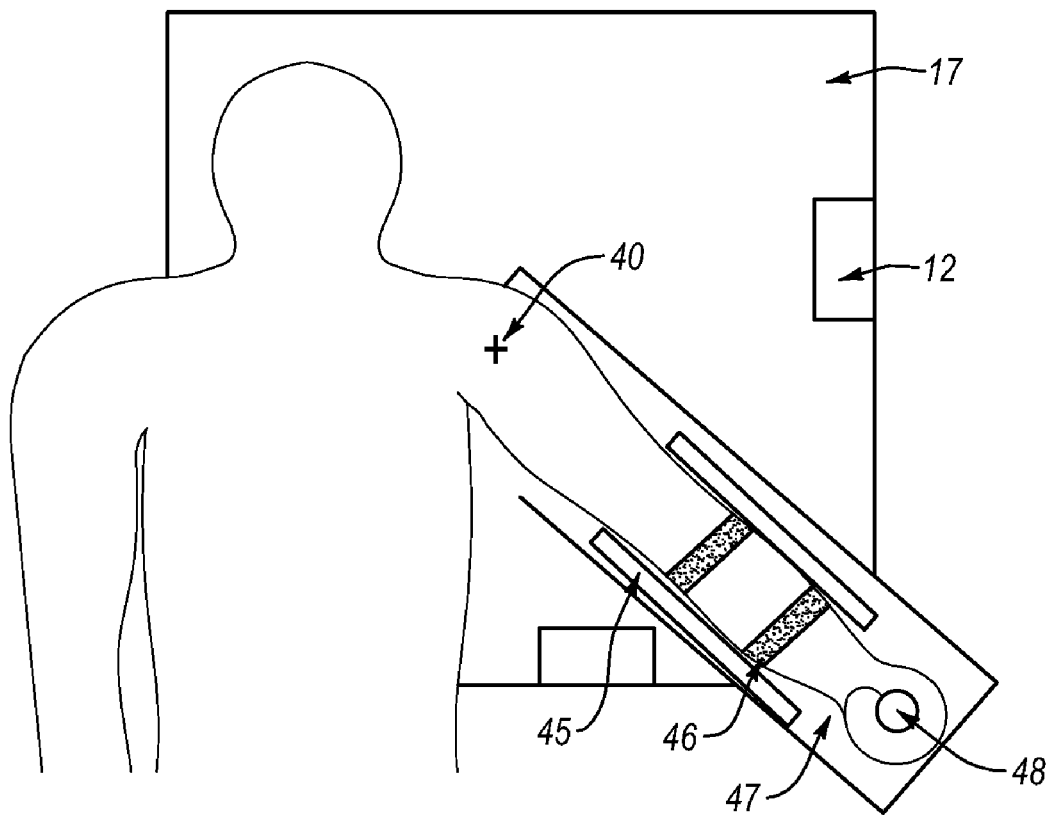
FIG. 9 is a front view of additional torque providing unit designed for shoulder joints abduction and adduction training of the present invention.

FIG. 9 is a front view of additional torque providing unit designed for shoulder joints abduction and adduction training of the present invention.

The additional torque providing unit 4 comprises: a mechanical arm 47 designed for training the shoulder joint and connected to the first coupling 21 via a nut; a support 45 fixed on the mechanical arm 47 for fixing patient's upper arm and forearm; a tieback 46 fixed on the support 45 for fixing patient's upper arm and forearm with the support together; a handle 48 fixed on the mechanical arm 43 for facilitating patient to grip; and the axis 40 shared by the first coupling 21, the second coupling 23, the torque sensor 22, the motor 15, the mechanical arm 47 for rotation.

Referring to FIG. 2-9, driven by the first coupling, the mechanical arms connect to the first coupling and are detachable, so the rehabilitation robotic system can be applied to the elbow (see FIG. 2-4), the wrist (see FIG. 5), the knee (see FIG. 6), the ankle (see FIG. 7), the shoulder (see FIG. 8-9) and other joints for rehabilitation training by using different mechanical arms. The mechanical arm, the panel and the base plate can be placed horizontally, which make the mechanical arm rotate in the horizontal surface for the elbow and wrist joints rehabilitation training. The mechanical arm, panel and base plate also can be placed vertically, which make the mechanical arm rotate in the vertical surface for the elbow and wrist joints rehabilitation training.

Figure 10:
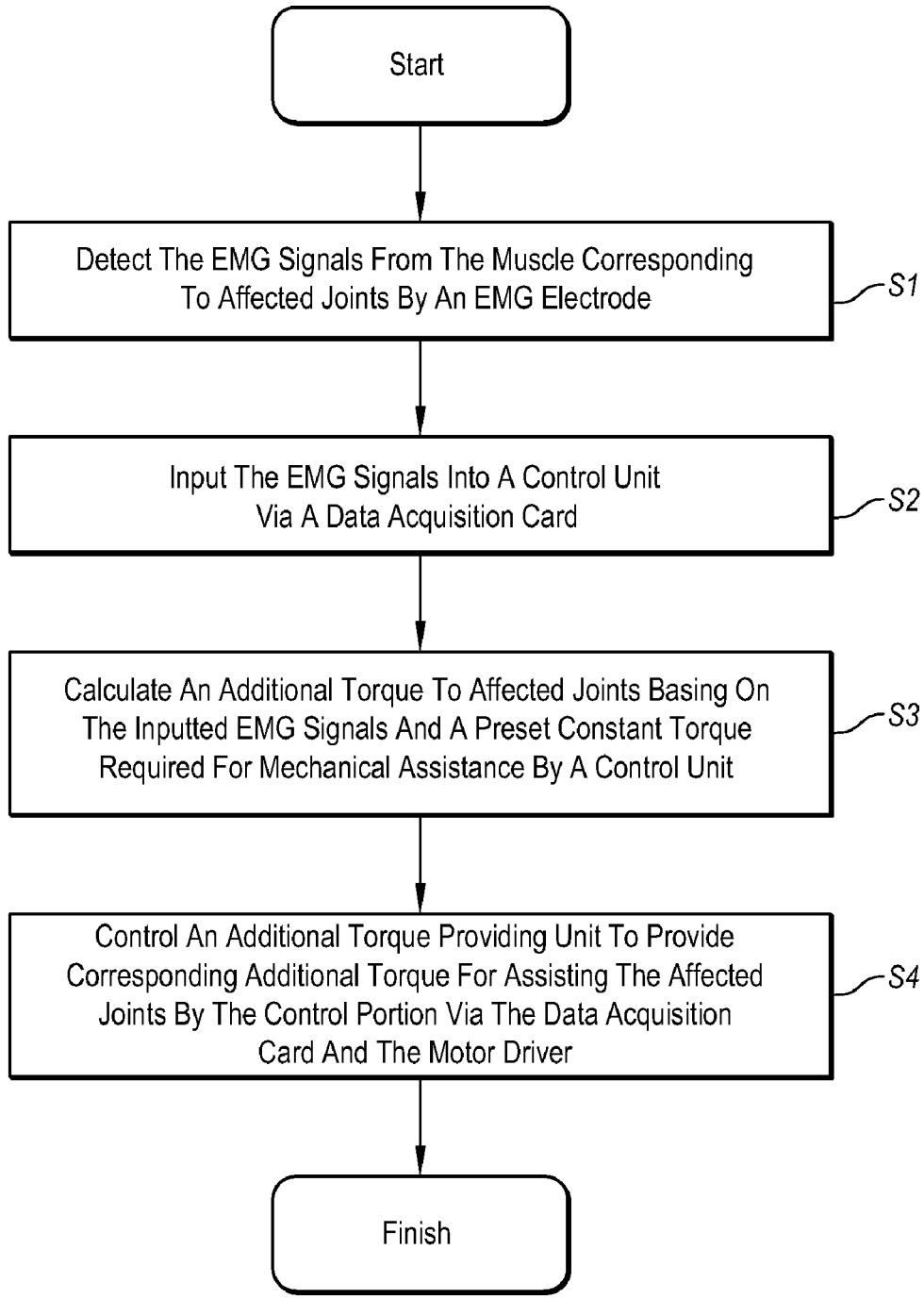
FIG. 10 is a flow chart of the method for providing mechanical help to patients by using EMG signals.

The method of providing patients mechanical help by using EMG signals of the present invention is illustrated with reference to FIG. 10 and the above description, and will not be repeated here.

According to Mortality and Morbidity Statistics of Hospital Authority Hong Kong in 2003, approximately 25,000 people suffered from stroke in Hong Kong and were admitted to the hospital. Our medical group is the first group in the world that has investigated the training effect of the EMG-controlled robotic on patients after stroke. Outcome measurements on the muscle strength at the elbow joint showed that there were increases in the muscle strength of the affected arms of all the patients after the four-week rehabilitation training. The patients could have a large range of motion for their affect elbow joint without the help of the robotic system after the four-week rehabilitation training. In addition, there were improvements in clinical scores after training, such as a decrease in the modified Ashworth scale and an increase in the Fugl-Meyer score.

The robotic system and training method for rehabilitation of this invention can capture patients' intention through the EMG signals from affected muscle, and provide the corresponding mechanical help and visual feedback. The system and the method can also assist the stroke patients join the rehabilitation training initiatively, and re-learn control muscle. Compared with the passive training to the patients in prior art, our system can train patients initiatively and provide them the visual feedback and the additional torque combined with the assistive torque and the resistive torque.

What is claimed is:

1. A robotic system for rehabilitation using electromyographic (EMG) signals to provide a mechanical help, comprising:
   an EMG electrode;
   a data acquisition card;
   a control unit connecting to said EMG electrode and said data acquisition card in series;
   a driver connecting to said data acquisition card;
   an additional torque providing unit connecting to said driver,
   wherein the EMG signals from the muscle corresponding to affected joints are detected by said EMG electrode, and inputted into said control unit via said data acquisition card; and
   based on the inputted EMG signals and a preset constant torque required for the mechanical help, an additional torque to the affected joints is calculated by said control unit and further is provided via said data acquisition card to said driver;
   said driver controls said additional torque providing unit to provide said additional torque for assisting the affected joints;
   wherein a normalized EMG signal (NEMG$_j$) is calculated by said control unit under the following equation (1):

$$NEMG_j = \frac{w_j - w_r}{w_{mvc} - w_r} \quad (1)$$

wherein, $w_j$ is an amplitude of rectified and filtered EMG signals created by the current acting of the affected joints' muscle, $w_r$ is an amplitude rectified and filtered EMG signals created by the affected joints' muscle at rest, $w_{mvc}$ is the rectified and filtered maximum amplitude of EMG signals created during maximal voluntary contraction of the affected joints' muscle;
   said additional torque $T_m$ is calculated by said control unit under the following equation (2):

$$T_m = K_1 \times NEMG_j - K_2 \times NEMG_i + T_0 \quad (2)$$

wherein, NEMG$_j$ is normalized EMG signal of an agonistic muscle of the affected joints' muscle, NEMG$_i$ is normalized EMG signal of an antagonistic muscle of the affected joints' muscle, $K_1$ is a weighting coefficient of the agonistic muscle, $K_2$ is a weighting coefficient of the antagonistic muscle, and $T_0$ is an additional constant torque that is provided according to requirement.

2. The system according to claim 1, further comprising:
   an amplifying and filtering circuit for rectifying and amplifying the EMG signals in full-wave, filtering with a moving window, and inputting into said data acquisition card.

3. The system according to claim 1, further comprising:
   an angle sensor fixed on said additional torque providing unit and connected to said data acquisition card for measuring the affected joints' angle and inputting said angle into said control unit via said data acquisition card; and
   a display unit connected to said control unit for displaying information of the affected joints' angles to patient.

4. The system according to claim 3, wherein said display unit further displays an objective angle to patient for displaying the affected joints' angle together with the objective angle.

5. The system according to claim 1, further comprising:
   a mechanical arm fixed on said additional torque providing unit for providing the additional torque; and
   a motor connected to said mechanical arm for rotating the mechanical arm.

6. The system according to claim 5, further comprising:
   a torque sensor fixed on said additional torque providing unit and electrically connected to said data acquisition card for detecting an interactive torque between said mechanical arm and said motor;
   a first coupling movably connecting said mechanical arm with one end of said torque sensor; and
   a second coupling connecting said motor with another end of said torque sensor,
   wherein said torque sensor, said first coupling, said second coupling, said mechanical arm and said motor all share a same axis.

7. An initiative rehabilitation training method for providing mechanical help using electromyographic (EMG) signals acquired from patients' affected side, such as elbows, wrists, knees, ankles and shoulders, said method comprising the steps of:
   detecting the EMG signals from the muscle corresponding to affected joints by an EMG electrode;
   inputting the EMG signals into a control unit via a data acquisition card;
   calculating an additional torque to the affected joints based on the inputted EMG signals and a preset constant torque required for mechanical help by the control unit and further providing said additional torque to a driver via said data acquisition card;
   controlling an additional torque providing unit to provide said additional torque for assisting the affected joints by said driver;
   wherein a normalized EMG signal (NEMG$_j$) is calculated by said control unit under the following equation (1):

$$NEMG_j = \frac{w_j - w_r}{w_{mvc} - w_r} \quad (1)$$

wherein, $w_j$ is an amplitude of rectified and filtered EMG signals created by the current acting of the affected joints' muscle, $w_r$ is an amplitude rectified and filtered EMG signals created by the affected joints' muscle at rest, $w_{mvc}$ is the rectified and filtered maximum amplitude of EMG signals created during maximal voluntary contraction of the affected joints' muscle;
   said additional torque $T_m$ in is calculated by said control unit under the following equation (2):

$$T_m = K_1 \times NEMG_j - K_2 \times NEMG_i + T_0 \quad (2)$$

wherein, NEMG$_j$ is normalized EMG signal of an agonistic muscle of the affected joints' muscle, NEMG$_i$ is normalized EMG signal of an antagonistic muscle of the affected joints' muscle, $K_1$ is a weighting coefficient of the agonistic muscle, $K_2$ is a weighting coefficient of the antagonistic muscle, and $T_0$ is an additional constant torque that is provided according to requirement.

8. The method according to claim 7, further comprising the steps of:

rectifying and amplifying the EMG signals in full-wave, filtering with a moving window, and inputting into said data acquisition card by a amplifying and filtering circuit.

9. The method according to claim 7, further comprising the step of:

measuring the affected joints angle by an angle sensor, and inputting said angle into said control unit via said data acquisition card; and displaying information of said affected joints' angles to patient on a display unit controlled by said control unit.

10. The method according to claim 9, wherein said display unit further displays an objective angle to patient for displaying the affected joints' angle together with the objective angle.

\* \* \* \* \*